United States Patent [19]

Fernholz et al.

[11] 3,980,671

[45] Sept. 14, 1976

[54] PROCESS FOR THE MANUFACTURE OF VINYL ACETIC ACID AND OPTIONALLY OF γ-BUTYROLACTONE

[75] Inventors: Hans Fernholz, Fischbach, Taunus; Dieter Freudenberger, Diedenbergen, Taunus, both of Germany

[73] Assignee: Hoechst Aktiengesellschaft, Frankfurt am Main, Germany

[22] Filed: Apr. 9, 1973

[21] Appl. No.: 348,992

[30] Foreign Application Priority Data

Apr. 12, 1972 Germany............................ 2217534
Jan. 27, 1973 Germany............................ 2303997

[52] U.S. Cl. .................... 260/343.6; 260/486 R; 260/526 N; 260/531 R; 260/532; 260/593 R; 260/595; 260/601 R; 260/614 AA
[51] Int. Cl.$^2$................ C07D 307/32; C07C 51/10
[58] Field of Search................. 260/343.6, 531, 532, 260/540, 531 R, 526 N

[56] References Cited

UNITED STATES PATENTS

| | | | |
|---|---|---|---|
| 3,061,614 | 10/1962 | Sweeney et al. | 260/343.6 |
| 3,437,676 | 4/1969 | von Kutepow et al. | 260/532 |
| 3,655,745 | 4/1972 | Fenton | 260/532 |
| 3,816,489 | 6/1974 | Craddock et al. | 260/532 |

OTHER PUBLICATIONS

Long et al. *The Reaction of Some π – Allylic Palladium Chloride Complexes with Carbon Monoxide, Journal of Chemical Society,* 1964, May pp. 1852–1853.

*Primary Examiner*—Natalie Trousof
*Assistant Examiner*—C. M. S. Jaisle
*Attorney, Agent, or Firm*—Curtis, Morris & Safford

[57] ABSTRACT

Vinylacetic acid and optionally γ-butyrolactone are prepared by reacting an allyl compound substituted by oxygen functions with carbon monoxide in the presence of a heavy metal catalyst. When the reaction is carried out with an allyl ether or a carboxylic acid allyl ester water is added. Vinylacetic acid is obtained in a very good yield in simple and economic manner.

17 Claims, No Drawings

PROCESS FOR THE MANUFACTURE OF VINYL ACETIC ACID AND OPTIONALLY OF γ-BUTYROLACTONE

The present invention relates to a catalytic process for the manufacture of vinyl acetic acid and optionally of γ-butyrolactone from oxygen-containing allyl compounds and carbon monoxide.

Methods for the manufacture of vinyl acetic acid are known. In general, vinyl acetic acid is produced by saponification of allyl cyanide with strong mineral acids. The main disadvantage of this method is the loss of the entire nitrile nitrogen in the form of useless ammonium salts, the disposal of which involves additional refuse problems.

Other possibilities to synthesize vinyl acetic acid are the hydrolysis of pyrrolidone with relatively low yields using a rather expensive starting material, which is not very economic, or the carboxylation of organo-metal compounds, for example allyl-lithium or diallyl-zinc or the like, which are rather sensitive.

According to a more recent process vinyl acetic acid can also be prepared by thermal isomerization of crotonic acid. But in this process a larger amount of isocrotonic acid is always obtained which is difficult to separate from the vinyl acetic acid by complicated and expensive crystallization processes.

There have also been proposed processes for the manufacture of vinyl acetic acid by carbonylation of π-allyl metal halide complex compounds or allyl halides, for example allyl chloride, in inert organic solvents. The main drawbacks of this process are the necessary removal of the halide moiety introduced with the allyl halide and the relatively complicated working up.

Knowing these older processes and methods it is quite obvious that the synthesis of vinyl acetic acid, in spite of its importance as organic intermediate product and monomer, causes considerable technical and economical difficulties.

The present invention provides a catalytic process for the manufacture of vinyl acetic acid and optionally of γ-butyrolactone by reacting allyl compounds substituted by oxygen functions with carbon monoxide, whereby the desired unsaturated carboxylic acid is obtained with a practically quantitative conversion and in a very good yield in a simple and economic manner.

The object of the invention is, therefore, a process for the manufacture of vinyl acetic acid and optionally of γ-butyrolactone which comprises reacting allyl alcohol, an allyl ether, or a carboxylic acid allyl ester with carbon monoxide in the presence of catalysts of heavy metals of subgroups VI, VII, and/or VIII of the Periodic Table according to Mendeleeff, in the case of allyl ether or carboxylic acid allyl ester the reaction being carried out in the presence of water.

When γ-butyrolactone is to be produced simultaneously, the reaction is preferably carried out with carboxylic acid allyl esters in the presence of water and a catalyst of subgroup VIII of the periodic Table with an excess of carbon monoxide.

The amount of lactone formed depends, in the first place, on the amount of water present. The formation of γ-butyrolactone is surprising as it is apparently not formed by cyclization of vinyl acetic acid, but by another reaction the mechanism of which is still unknown.

Suitable heavy metal catalysts are the elements molybdenum, tungsten, manganese, rhenium, iron, cobalt, nickel, ruthenium, rhodium, palladium, iridium, and platinum, as well as mixtures and compounds thereof, either individually or in any combination.

Preferred catalysts are cobalt, nickel, rhodium, and palladium, in the form of their halides, preferably the hydrated chlorides and iodides, or the carbonyls.

As allyl esters there are preferably used those in which the acid radical does not contain an olefinic or acetylenic bond and derives from a saturated aliphatic carboxylic acid having of from 2 to 18 carbon atoms in the molecule, or from an aromatic carboxylic acid having of from 7 to 11 carbon atoms in the molecule. Allyl acetate, allyl propionate and allyl isobutyrate are especially preferred since they are readily accessible.

Owing to the fact that catalytic amounts of the catalysts are used, which can be recovered after the reaction and reused, the process of the invention is not only very simple but also very economic and with a high selectivity and excellent total yield.

As compared with known processes, the process of the invention has the advantage that neither gaseous nor solid corrosive waste products, such as, for example, HCl or $NH_4Cl$, are formed and that a separate working up of a solvent can be dispensed with.

γ-Butyrolactone obtained by the process of the invention is used as starting material for the manufacture of polyesters.

The starting components used in the process of the invention, i.e., allyl component and carbon monoxide, are reacted with one another in equimolar or in non-stoichiometric proportion. In general, carbon monoxide is used in a larger molar excess, whereby the degree of conversion as well as the yield are considerably improved. To increase the local molar concentration of carbon monoxide the reaction is mostly carried out under elevated pressure. The limits of the pressure range to be maintained are very wide; they vary between 0.5 and 500 atm/g, preferably between 20 and 250 atm/g, more preferably above 80 atm/g.

The reaction temperatures required for obtaining acceptable reaction speeds and conversion rates at which a noteworthy decomposition or rearrangement of starting material and final product is not yet observed is, in general, in the range of from 50° to 300°C, especially 110° to 160°C.

In spite of the high sensitivity of vinyl acetic acid to rearrangement reactions, it is surprising that in the process of the invention isomeric $C_4$ acid, such as cis- and transcrotonic acid, are not formed or form in a small amount only, in contrast to known processes.

The reaction periods can be varied to a certain extent and depend on the pressure, temperatures and starting material. In general, a satisfactory conversion rate is obtained with residence times of from 10 minutes to 20 hours, preferably 5 to 10 hours under optimum pressure and temperature conditions as defined above.

The reaction can be carried out discontinuously as well as continuously. The catalysts used are either dissolved homogeneously in the reaction mixture or suspended heterogeneously, or supported on suitable carriers. With a discontinuous performance of the reaction the reaction vessel or autoclave is preferably equipped with stirring means to provide for a sufficient mixing of gaseous and liquid phase. When the reaction is performed in continuously operating reactors the turbulence and flowing conditions ensure a sufficient mixing of the reaction components and a favorable residence time, which may, however, be further improved by a special design or filling of the reactor. With continuous as well as discontinuous operation the unreacted carbon monoxide, which is mostly used in a large molar excess, can be recycled into the reaction after separation from reaction mixture, whereby the economy of the process is further improved.

The reaction can be carried out in the liquid phase as well as in gaseous or vaporous phase provided that the partial pressures are kept correspondingly low, working in the liquid phase being preferred.

The catalysts are generally used in an amount of from 0.02 to 5 grams of metal or metal compound per mol of allyl component. Special catalyst combinations have proved advantageous; they surprisingly increase the reaction rates and the yield of vinyl acetic acid. More particularly, the reaction is promoted by the addition of iodine containing compounds, for example methyl iodide, as cocatalysts, or by the direct use of the heavy metals in the form of their iodides, preferably iodide hydrates. Simultaneously, the formation of undesired by-products is suppressed.

A combination of $RhCl_3 . H_2O$ with $CH_3I$, for example, increases the yield of vinyl acetic acid 2 to 3 times, the mixture of $Ni(CO)_4$ with $CH_3I$ even more than 20 times over the yield obtained with the individual components, while simultaneously a smaller amount of rearrangement products and high boiling by-products is obtained. Other combinations, too, promote the reaction in the same sense, for example the combination of $RhCl_3 . H_2O$ with $PdI_2$. The amount of the cocatalyst corresponds to generally 0.5 to 20 times, preferably 5 to 8 times, the amount of the principal catalyst.

$CH_3I$ as co-catalyst is used, for example, in an amount of from 0.25 to 10 grams, preferably 1 to 5 grams, and more preferably 3.5 grams, on the average, for one mol of allyl compound, while the catalyst is used in an amount of from 0.05 to 5 grams, preferably 0.05 to 1 grams and more preferably 0.1 to 0.6 gram.

When allyl alcohol, especially, however, allyl ethers, for example diallyl ether, or allyl esters of carboxylic acids, for example allyl acetate or allyl propionate, are used, the presence of water has proved advantageous. In general, 0.01 to 20 mols, preferably 2 to 5 mols of $H_2O$ are used for each mol of allyl compound.

The most favorable way to work up the reaction mixture is by fractional distillation, optionally under reduced pressure.

Depending on the type of the starting material and the reaction products obtained, part of the separated compounds may be reused. Thus, it is possible to use the acetic acid formed from allyl acetate or the propionic acid formed from allyl propionate, if desired in the form of dilute aqueous acid, for producing the allyl carboxylic acid ester according to known processes. This constitutes a further advantage of the process of the invention over the known processes, in which, for example, alkenyl halides are used as starting material, and a direct recirculation of the split-off chlorine is not possible.

When catalysts supported on carriers are used in the process of the invention, suitable carrier materials are, for example, silicium dioxide, aluminium oxides, active carbon, zirconium oxide, aluminium silicates, and molecular sieves, $SiO_2$ being preferred.

Especially good results are obtained when vinyl acetic acid and optionally γ-butyrolactone are produced from allyl oxygen compounds and carbon monoxide in the following manner:

A mixture of allyl alcohol, rhodium chloride hydrate and nickel iodide are introduced into a shaking autoclave, the autoclave is closed and gaseous carbon monoxide is metered in through a separate conduit. The reaction mixture is shaken continuously while heating whereby the pressure rises automatically. A slight drop in pressure recorded on the manometer and due to the progression of the reaction is compensated by adding carbon monoxide. The reaction is interrupted after about 6 hours, the reaction mixture is cooled to room temperature and the pressure in the autoclave is released. The reaction solution obtained is worked up by fractional distillation.

The following examples illustrate the invention.

EXAMPLE 1

58 grams (1 mol) of allyl alcohol, 0.5 g of $RhCl_3 . H_2O$, 3.5 grams of $NiI_2 . 6 H_2O$ and 6 grams of water were introduced into a 6 liter shaking autoclave made of stainless steel. 125 atm/g of carbon monoxide were forced in, the mixture was heated at 138° – 140°C whereby the pressure automatically rose to about 150 atm/g.

After shaking for about 6 1/2 hours the experiment was interrupted, the reaction solution cooled and the pressure released. 85 grams of reaction solution were obtained having the following composition:

| | | |
|---|---|---|
| 85 % | ≙ 72.2 g | vinyl acetic acid |
| <0.1 % | <0.1 g | vinyl acetic acid allyl ester |
| <0.1 % | <0.1 g | diallyl ether |
| <0.5 % | <0.5 g | propionaldehyde |
| <0.5 % | <0.5 g | acetone |
| 1.1 % | ~1 g | water |
| 5.3 % | 4.5 g | allyl alcohol |
| 7.2 % | 6.1 g | catalyst and unknown components |

The yield of vinyl acetic acid amounted to about 84 % of the theory.

EXAMPLE 2

58 grams (1 mol) of allyl alcohol, 0.5 g of rhodium chloride hydrate and 3.5 grams of methyl iodide were given into a 1 liter tantalum shaking autoclave. The autoclave was pressurized with 150 atm/g of carbon monoxide and heated at 135°C while continuously shaking. After a reaction time of 7½ hours, the reaction mixture was cooled, the pressure was released and the mixture analyzed by gas chromatography. 80.9 grams of reaction solution were composed of

| | | |
|---|---|---|
| 74.2 % | ≙ | 60.1 g vinyl acetic acid |
| 9.2 % | ≙ | 7.5 g vinyl acetic acid allyl ester |
| 3.3 % | ≙ | 2.7 g diallyl ether |
| 1.2 % | ≙ | 1.0 g propionaldehyde |
| 4.3 % | ≙ | 3.5 g allyl alcohol | about 7.8 % = about 6.3' g unknown components and catalyst

The amount of 60.1 grams of vinyl acetic acid obtained corresponded to a yield of about 70 % of the theory.

EXAMPLE 3

1 mol (58 grams) of allyl alcohol was introduced into a 1 liter tantalum autoclave, 1 gram of $RhI_3$ was added, the autoclave was pressurized with 140 atm/g of carbon monoxide, and heated at 125°C. After about 5 1/2 hours the reaction was interrupted. 83 grams of reaction mixture were obtained having the following composition:

|       | 83 % = | 69 g   | vinyl acetic acid |
|-------|--------|--------|-------------------|
| about | 1.4 %  | 1.2 g  | vinyl acetic acid allyl ester |
| about | 0.5 %  | ~0.4 g | acetone, diallyl ether propionaldehyde |
|       | 9.6 %  | ~8 g   | allyl alcohol |
| about | 4.8 % =| 4.0 g  | catalyst and unknown components |

69 grams of vinyl acetic acid corresponded to a yield of about 80 % of the theory.

EXAMPLE 4

An autoclave as used in Example 1 was charged with 58 grams (1 mol) of allyl alcohol, 0.2 gram $RhCl_3 \cdot H_2O$ and 1 g $PdI_2$, pressurized with CO to a pressure of about 150 atm/g and heated at 125° – 135°C. The reaction was interrupted after about 6 hours and the cooled mixture analyzed. 81 grams of reaction solution were obtained containing 70 % (57 grams) of vinyl acetic acid, corresponding to a yield of 66 – 67 %.

EXAMPLE 5

A 1 liter shaking autoclave made of stainless steel was charged with 1 mol (100 grams) of allyl acetate, 0.5 gram $RhCl_3 \cdot 3 H_2O$, 1 gram $Ni(CO)_4$ and 18 grams of water, the autoclave was pressurized with 145 atm/g carbon monoxide and the mixture heated at 138° – 140°C. After a time of reaction of 7 hours the reaction was interrupted and the mixture analyzed. 98 grams of reaction mixture were obtained containing about 15 % of vinyl acetic acid. Diallyl ether and vinyl acetic acid allyl ester were not formed. Besides acetic acid the mixture further contained the unreacted allyl acetate, small amounts of allyl alcohol, a little propionaldehyde and high boiling constituents.

EXAMPLE 6

A 1 liter shaking autoclave made of tantalum was charged with 1 mol of diallyl ether (98 grams), 0.5 g $RhCl_3 \cdot H_2O$, 3.5 grams $CH_3I$, and 50 grams of water. The autoclave was pressurized with 135 atm/g carbon monoxide and heated at 135° – 140°C.

After a reaction time of 6½ hours the autoclave was cooled, the pressure released and the reaction mixture having a weight of 173 grams was analyzed. The mixture contained 45 grams of vinyl acetic acid, corresponding to a yield of 53 % of the theory.

EXAMPLE 7

Into the upper end of a vertically arranged high pressure tube reactor made of stainless steel, having a length of 55 cm, an inner diameter of 3 cm and an empty volume of about 0.5 liter, provided with heating means and filled half with glass balls, 100 ml of a mixture consisting of 58 grams allyl alcohol, 0.5 g $RhCl_3 \cdot H_2O$ and 3.5 grams $CH_3I$ were introduced per hour while 5 to 10 mols/hour of CO were continuously pumped in at the lower end under a constant pressure of 123 atm/g and at 120° – 135°C. The reaction mixture withdrawn at the lower end of the reactor after a mean residence time of about 5 hours was analyzed. It contained on the average between 47 and 71 % of vinyl acetic acid. The unreacted carbon monoxide was taken off at the upper end of the reactor over a cooler system maintained under pressure in such a way that the adjusted pressure was in the range of from 120 to 130 atm/g on the average.

EXAMPLE 8 (Comparative example)

The reaction was carried out as described in Example 1 with the exception that no $CH_3I$ was used. The pressure amounted to about 127 atm/g, the inside temperature was 105°C. After a reaction time of 7½ hours 54 grams of reaction mixture were obtained having the following composition:

| 25 % | = | 13.5 g | vinyl acetic acid |
| 18 % | = | 9.72 g | vinyl acetic acid allyl ester |
| 25 % | = | 13.5 g | propionaldehyde and acetone |
| 10 % | = | 5.4 g  | allyl alcohol |
| 15 % | = | 8.1 g  | diallyl ether |
| 7 %  | = | 3.8 g  | unknown components |

The yield of vinyl acetic acid was scarcely 16 %. Additionally, an undefined amount of $CO_2$ and propylene formed which was lost, as well as a small amount of water.

EXAMPLE 9

100 grams of allyl acetate, 1 gram of rhodium iodide and 200 grams of water were introduced into a 1 liter shaking autoclave lined with tantalum. The autoclave was pressurized with 143 atmospheres carbon monoxide and the mixture was heated within 40 minutes at 142°C while continuously shaking. The experiment was interrupted after 115 minutes, the reaction mixture rapidly cooled and released to atmospheric pressure. The reaction solution contained 27 grams of γ-butyrolactone and 13 grams of vinyl acetic acid.

EXAMPLE 10

200 grams of allyl acetate, 360 grams of water, 1 gram $RhCl_3 \cdot H_2O$ and 2 grams $NiI_2 \cdot 6 H_2O$ were introduced into a 1 liter shaking autoclave made of stainless steel. The autoclave was pressurized with 126 atmospheres carbon monoxide and rapidly heated at 145°C while shaking. After 2 hours the reaction mixture was cooled and analyzed. 51.6 grams of γ-butyrolactone and 20.6 grams of vinyl acetic acid were obtained.

EXAMPLE 11

114 grams of allyl propionate, 162 grams of water and 0.9 gram of palladium chloride were introduced into a 1 liter stainless steel shaking autoclave. The autoclave was pressurized with 160 atmospheres carbon monoxide, heated at 159°C and the temperature was maintained for 65 minutes. After cooling and pressure release the reaction solution was analyzed by gas chromatography. It contained 18.7 grams of γ-butyrolactone and 11 grams of vinyl acetic acid.

EXAMPLE 12

The reaction was carried out as described in Example 11, with the exception that 128 grams of allyl isobutyrate were used instead of allyl propionate. 19.1 grams of γ-butyrolactone and 10.6 grams of vinyl acetic acid were obtained.

EXAMPLE 13

The reaction was carried out as described in Example 11, with the exception that 156 grams of allyl caproate were used instead of allyl propionate. 16.6 grams of γ-butyrolactone and 11.8 grams of vinyl acetic acid were obtained.

EXAMPLE 14

100 grams of allyl acetate were reacted with carbon monoxide as described in Example 9, however in the presence of 4 grams $H_2IrCl_6$ instead of $RhI_3$. Gas chromatographic analysis indicated a yield of 6.2 grams of γ-butyrolactone and 10.2 grams of vinyl acetic acid.

EXAMPLE 15

In a 1 liter tantalum autoclave 162 grams of allyl benzoate, 180 grams of water and 25 grams of a supported catalyst containing 1.65 grams of rhodium chloride on 100 grams of active carbon, were shaken for 45 minutes at 145°C under a carbon monoxide pressure of 140 atm/g. Next, the reaction mixture was cooled, the pressure was released and the mixture was analyzed by gas chromatography. It contained 22.3 grams of γ-butyrolactone and 9 grams of vinyl acetic acid.

EXAMPLE 16

The reaction was carried out as described in Example 15, with the exception that 170 grams of the allyl ester of p-toluylic acid were used instead of the benzoate. 21.2 grams of γ-butyrolactone and 8.8 grams of vinyl acetic acid were obtained.

What is claimed is:

1. A process for the manufacture of vinyl acetic acid comprising the step of reacting allyl ether, allyl ester of saturated aliphatic carboxylic acid of 2 to 18 carbon atoms or allyl ester of aromatic carboxylic acid of 7 to 11 carbon atoms with carbon monoxide to form vinyl acetic acid, the reaction being conducted at a pressure of about 0.5 to about 500 atmospheres (gauge) and a temperature of about 50°C. to about 300°C. in the presence of about 0.02 to about 5 grams per mol of said allyl compound of a catalyst that is molybdenum, tungsten, manganese, rhenium, iron, cobalt, nickel ruthenium, rhodium, palladium, osmium, iridium, platinum or a carbonyl or halide compound of one of said metals, and about 0.01 to about 20 mols of water per mol of said allyl compound, and separating the formed vinyl acetic acid and from the reaction mixture.

2. A process according to claim 1 wherein said pressure is about 20 to about 250 atmospheres (gauge).

3. A process according to claim 1 wherein said pressure is greater than about 80 atmospheres (gauge).

4. A process according to claim 1 wherein said temperature is about 110°C. to about 160°C.

5. A process according to claim 1 wherein about 2 to about 5 mols of water are used per mol of allyl compound.

6. A process according to claim 1 wherein said halide compound is a chloride or an iodide.

7. A process according to claim 1 wherein said allyl ether is diallyl ether.

8. A process according to claim 1 wherein said allyl ester is allyl acetate, allyl propionate, allyl isobutyrate, allyl caproate, allyl benzoate or allyl-p-toluylate.

9. A process according to claim 1 wherein said allyl ester is allyl acetate, allyl propionate or allyl isobutyrate.

10. A process according to claim 1 wherein about 0.05 gram of catalyst is used.

11. A process according to claim 1 wherein said reaction is conducted in the presence of a co-catalyst that is a catalytically active iodide.

12. A process according to claim 11 wherein said co-catalyst is used in an amount of about 0.5 to about 20 times the amount of said catalyst.

13. A process according to claim 11 wherein said co-catalyst is used in an amount of about 5 to about 8 times the amount of said catalyst.

14. A process according to claim 11 wherein said co-catalyst is methyl iodide, nickel iodide or palladium iodide.

15. A process according to claim 11 wherein said catalyst and co-catalyst are $RhCl_3.H_2O$ and $CH_3I$, $Ni(CO)_4$ and $CH_3I$, $RhCl_3.H_2O$ and $PdI_2$, or $RhCl_3.H_2O$ and $NiI_2.6H_2O$.

16. A process according to claim 1 wherein said allyl ester of saturated carboxylic acid is reacted in excess carbon monoxide and additional water of about 3 to about 30 mols for the manufacture of gamma-butyrolactone simultaneously with said vinyl acetic acid.

17. A process according to claim 16 wherein said catalyst is rhodium, palladium, nickel, iridium, platinum or cobalt.

* * * * *